US00PP12865P2

(12) United States Plant Patent
Noodelijk

(10) Patent No.: US PP12,865 P2
(45) Date of Patent: Aug. 20, 2002

(54) CHRYSANTHEMUM NAMED 'CURRANT ELGON'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/562,281

(22) Filed: May 1, 2000

(51) Int. Cl.[7] ..... A01H 5/00
(52) U.S. Cl. ..... Plt./298
(58) Field of Search ..... Plt./298

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A Chrysanthemum plant named 'CURRANT ELGON' characterized by its medium sized blooms with dark salmon ray-florets and yellow-green disc florets.

2 Drawing Sheets

RELATED CULTIVARS

'CURRANT ELGON' is related to 'DARK PINK ELGON' (U.S. plant patent application Ser. No. 09/562,281) and 'ELGON' (U.S. plant patent application Ser. No. 09/276,697). 'CURRANT ELGON' and 'DARK PINK ELGON' are color mutants of 'ELGON'.

BACKGROUND OF THE INVENTION

'CURRANT ELGON' is a product of a breeding and selection program which had the objective of finding color mutants of 'ELGON'. The new plant of the present invention comprises a new and distinct cultivar of chrysanthemum plant that is a natural occuring sport of a parent chrysanthemum named 'ELGON'. A comparison with Parent chrysanthemum 'ELGON' is also made in this application. The new cultivar was discovered as a whole plant mutation in April 1998 by Rob Noodelijk in a controlled environment (greenhouse) in Rijsenhout Holland. The first act of asexual reproduction of 'CURRANT ELGON' was accomplished when vegetative cuttings were taken from the initial selection in August 1998 in Rijsenhout Holland.

SUMMARY OF THE INVENTION

The present invention is a new and distinct variety of chrysanthemum bearing medium sized blooms with dark salmon ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
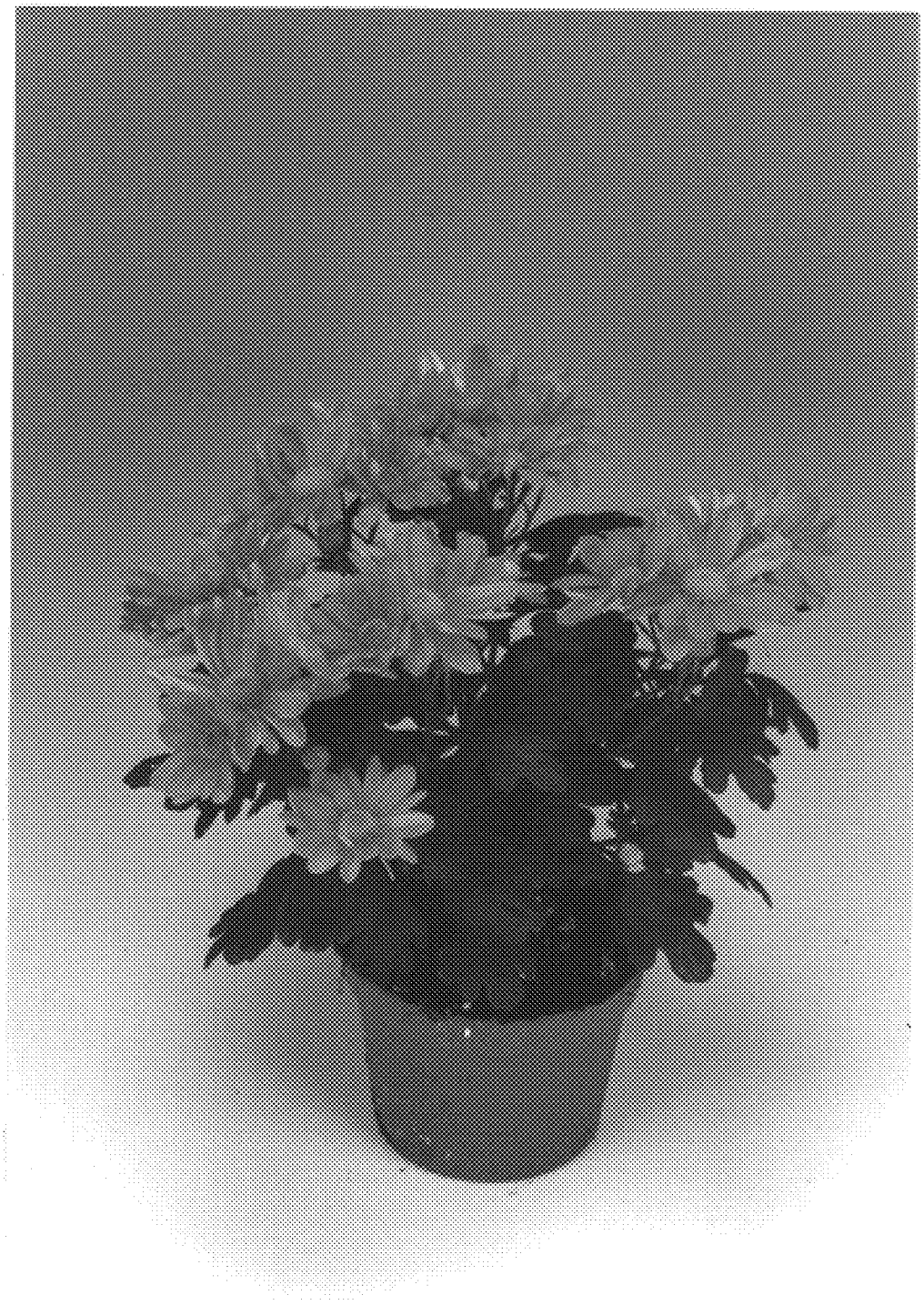
FIG. 1 shows a plant of the cultivar in full bloom.
Figure 2:
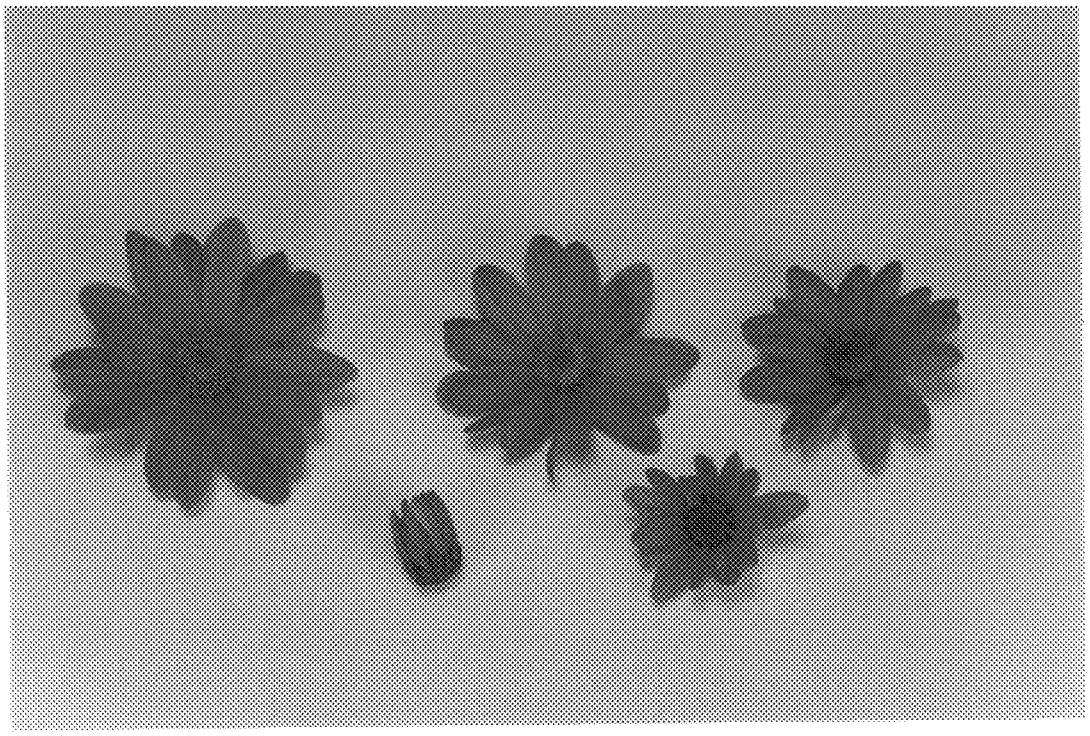
FIG. 2 shows the various stages of bloom of the new cultivar.
Figure 3:
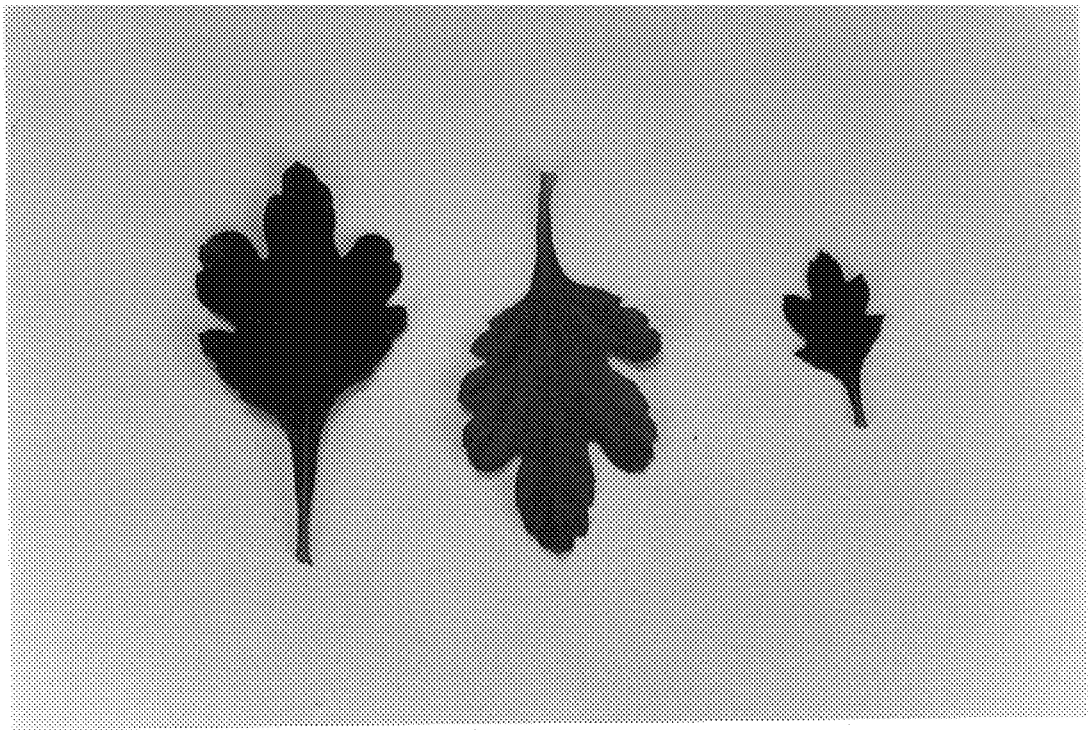
FIG. 3 shows the various stages of foliage and petiole of the new cultivar.

This new variety of chrysanthemum is of the botanical classification dendranthema grandiflora. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 50 days after an average of eight long days. After this long day period to flowering growth retardants were applied 6 times in an average dose of 1.5 gram/liter water. The plants were observed (directly) during the flowering of this crop. No tests were done on disease or insect resistance or susceptibility. No tests were done on cold of drought tolerance. This new variety produces medium sized blooms with dark salmon ray-florets and yellow-green disc-florets blooming on the plant for 4 weeks. This new variety of chrysanthemum has been found to retain its distinctive characteristics throughout successive propagations however the phenotype may vary significantly with variations in environment such as light intensity and temperature. To show the phenotype as described 'CURRANT ELGON' may be planted without assimilation lightning (high pressure sodium lamps) between week 50 and 40 of the next year under greenhouse conditions in Holland. With assimilation lightning (minimum level 2500 lux) it may be planted year round under greenhouse conditions in Holland.

From the cultivars known to inventor the most similar existing cultivar in comparison to 'CURRANT ELGON' is 'ELGON' and 'DARK PINK ELGON'. When 'ELGON' and 'DARK PINK ELGON' are being compared the following differences and similarities are noticed: The difference of 'ELGON', 'CURRANT ELGON' and 'DARK PINK EGLON' is the ray-floret color for which characteristics 'CURRANT ELGON' and 'DARK PINK ELGON' are selected out of 'ELGON'. 'CURRANT ELGON' is salmon, 'DARK PINK ELGON' is dark pink, 'ELGON' is pale pink. All other characteristics of 'CURRANT ELGON', 'ELGON' and 'DARK PINK ELGON' are similar.

The following is a description of 58 day old the plant and characteristics that distinguish 'CURRANT ELGON' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

*Dendranthema grandiflora* 'CURRANT ELGON'

Bud:
*Size.*—Medium, cross-section 1.2 cm height 0.9 cm.
*Outside color.*—Red 48 B.
*Involucral bracts.*—2 rows, length 7 mm, width 3 mm.
*Involucral bracts among disc-florets.*—Not present.
*Involucral bracts color.*—Yellow-green 144 A.

Bloom:
*Type.*—Single.
*Height.*—Flat.
*Size.*—Medium.
*Fully expanded.*—6.0–6.5 cm.
*Borne* (*number of blooms per branch*).—Approx. 4–5 blooms per branch.
*Performance on the plant.*—4 weeks.
*Seeds.*—Not produced.
*Fragrance.*—Typical chrysanthemum.

Color:
*Center of the flower* (*disc-florets*).—Immature yellow-green 151 A, mature green-yellow 1 B.
*Color of upper surface of the ray-florets.*—Red 51 B.
*Color of the lower surface of the ray-florets.*—Red 48 B.
*Tonality from distance.*—A pot mum with purple daisy flowers and a yellow-green disc.
*Discoloration to color.*—Red 51 D.

Ray florets:
*Texture.*—Upper side and under side smooth.
*Number.*—20–24.
*Cross-section.*—Flat.
*Longitudinal axis of majority.*—Flat.
*Length of corolla tube.*—Short.
*Ray-floret length.*—2.2–2.5 cm.
*Ray-floret width.*—0.7–1.0 cm.
*Ratio length/width.*—Low.
*Shape of tip.*—Rounded.

Disc florets:
*Disc diameter.*—1.5 cm.
*Distribution of disc florets.*—Numerous, clearly visible at all stages of flowering.
*Shape.*—Tubular.
*Color.*—Yellow-green 151 A.
*Receptacle shape.*—Conicul raised.

Reproductive organs:
*Stamen* (*present in disc florets only*).—Thick, 3 mm length.
*Number of stamen.*—Grown together as one.
*Stamen color.*—Yellow-green 144 B.
*Pollen.*—Present, abundant.
*Pollen color.*—Yellow 12 A.
*Styles* (*present in both ray and disc*).—Thin.
*Style color.*—Yellow-green 144 B.
*Style length.*—4 mm.
*Stigmas.*—Yellow-green 144 B.
*Stigma width.*—2 mm.
*Ovaries.*—Enclosed in calyx.

Plant:
*Type.*—A pot mum meant for indoor use.
*Growth habit.*—Spreading.
*Growth rate.*—Slow.
*Height.*—20.0–22.0 cm.
*Width.*—23.0–25.0 cm.
*Stem color.*—Yellow-green 144 A.
*Stem strength.*—Medium.
*Stem brittleness.*—Present.
*Stem anthocyanin coloration.*—Absent.
*Length of lateral branch.*—11–13 cm.
*Lateral branch, attachment.*—Weak, a little brittle.
*Branching* (*average number*).—Normal, with 3–4 breaks after pinching.
*Peduncle length.*—2.0–3.0 cm.
*Peduncle color.*—Yellow-green 144 A.
*Flowering response* (*photo-periodic controlled crop, not natural season*).—50 days.

Foliage:
*Color.*—Upper side yellow-green 147 A, Under side Yellow-green 147 B.
*Size.*—Medium; length 6.0 cm, width 4.5 cm.
*Quantity* (*number per lateral branch*).—6–8.
*Shape.*—Round.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Attenuate.
*Apex.*—Mucronate.

Differences with the comparison Varieties

| | 'CURRANT ELGON' | 'DARK PINK ELGON' | 'ELGON' |
|---|---|---|---|
| Ray-floret color | Red 51 B | Red-purple 67 B | Red-purple 73 B |

I claim:

1. A new and distinct variety of chrysanthemum plant as described and illustrated.

* * * * *